United States Patent
Sato et al.

(10) Patent No.: US 7,365,853 B2
(45) Date of Patent: Apr. 29, 2008

(54) MEASURING METHOD AND MEASURING APPARATUS UTILIZING ATTENUATED TOTAL REFLECTION

(75) Inventors: Shu Sato, Kanagawa-ken (JP);
Toshihito Kimura, Kanagawa-ken (JP);
Hisashi Ohtsuka, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 33 days.

(21) Appl. No.: 11/239,305

(22) Filed: Sep. 30, 2005

(65) Prior Publication Data
US 2006/0066861 A1    Mar. 30, 2006

(30) Foreign Application Priority Data
Sep. 30, 2004    (JP) ............................. 2004-288105

(51) Int. Cl.
*G01N 21/55*    (2006.01)
(52) U.S. Cl. ..................................... 356/445
(58) Field of Classification Search ................. 356/445
See application file for complete search history.

(56) References Cited

U.S. PATENT DOCUMENTS 5,508,809 A * 4/1996 Peacock et al. ............. 356/445
2002/0149775 A1 * 10/2002 Mori et al. .................. 356/445
2004/0130723 A1 * 7/2004 Yager et al. ................ 356/445

FOREIGN PATENT DOCUMENTS

JP    6167443 A    6/1994
JP    7159319 A    6/1995

OTHER PUBLICATIONS

"Surface Refracto-sensor using Evanescent Waves: Principles and Instruments" by Takayuki Okamoto, Spectrum Researches, vol. 47, No. 1 (1998), pp. 21-23 and pp. 26-27.

* cited by examiner

*Primary Examiner*—Tarifur Chowdhury
*Assistant Examiner*—Tara S Pajoohi
(74) *Attorney, Agent, or Firm*—Sughrue Mion, PLLC

(57) ABSTRACT

A measurement path is filled with air prior to performing actual measurement. A p-polarized light beam is caused to enter an interface, and the intensity distribution of the light beam reflected at the interface is detected by a photodiode array to obtain a reference intensity distribution of the light beam itself. Thereafter, the measurement path is filled with a target for measurement, and the intensity distribution of a light beam reflected at the interface is measured. Each of the measured distribution values are divided by the reference intensity distribution, to cancel out influences due to fluctuations in the intensity distribution of the light beam. Thereby, the position of an attenuated total reflection angle is detected with high accuracy. Because a light beam constituted by p-polarized light waves is utilized, separating means for separating the light beam reflected at the interface into p-polarized and s-polarized light waves becomes unnecessary.

11 Claims, 7 Drawing Sheets

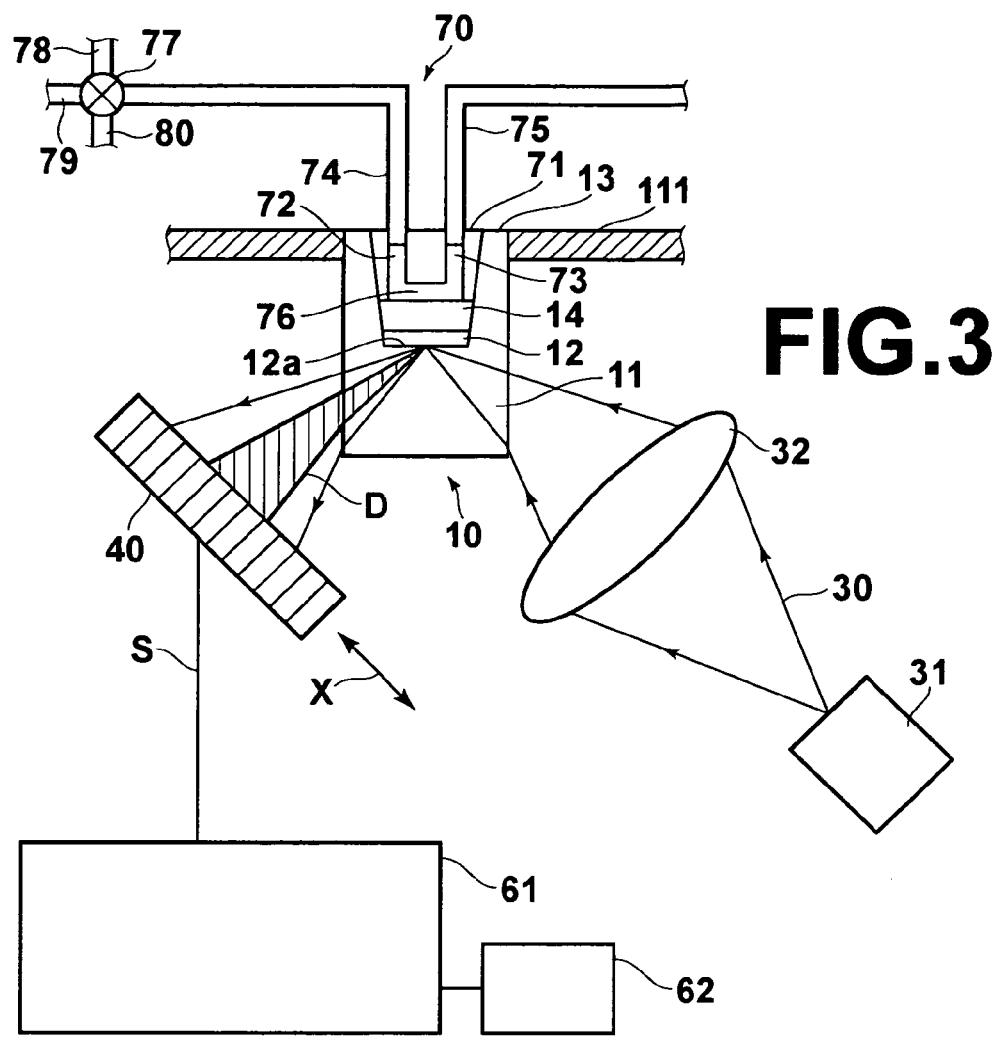

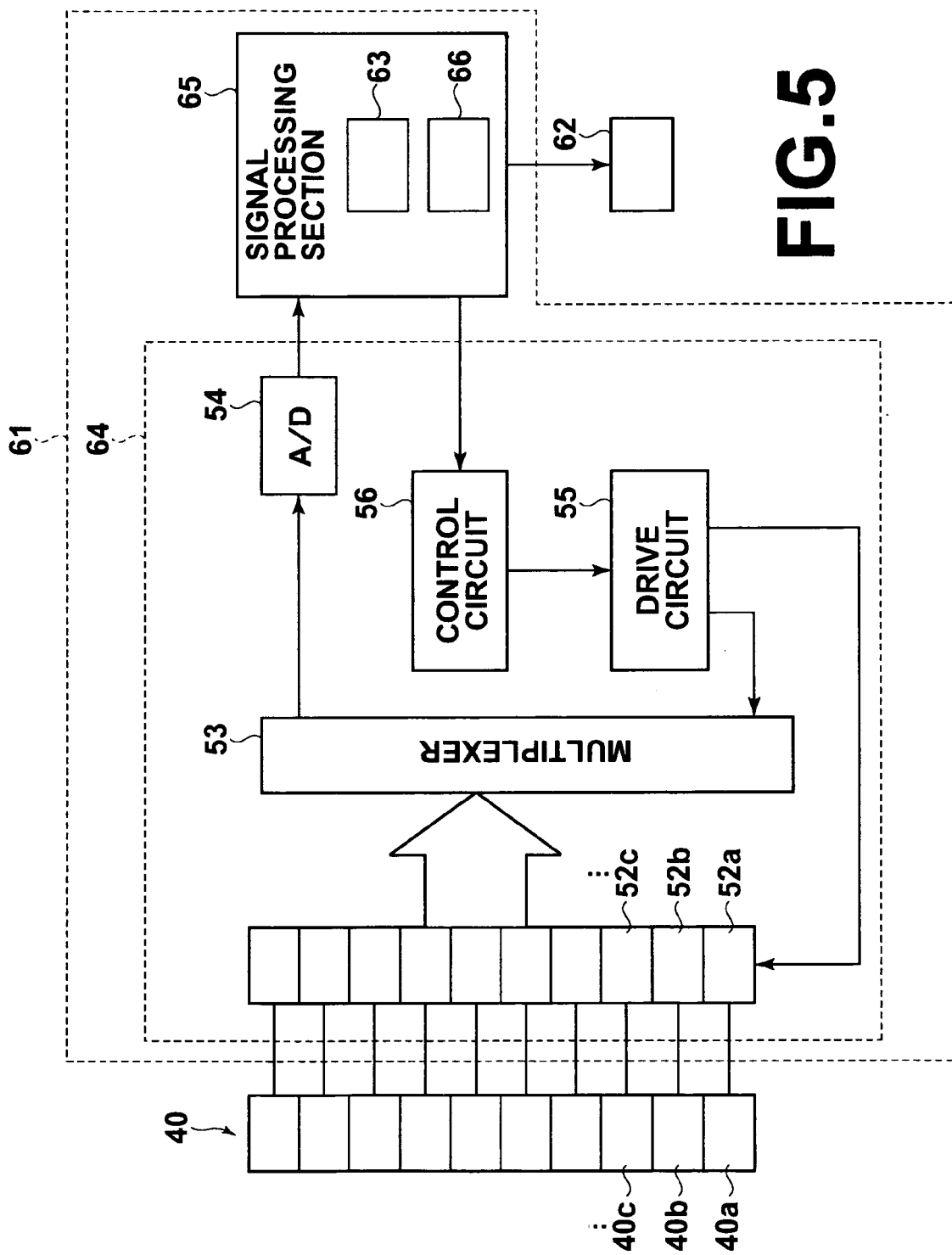

ANGLE ON INCIDENCE θ

ANGLE ON INCIDENCE θ

ANGLE ON INCIDENCE θ

ANGLE ON INCIDENCE θ

MEASURING METHOD AND MEASURING APPARATUS UTILIZING ATTENUATED TOTAL REFLECTION

BACKGROUND OF THE INVENTION

1. Field of the Invention

The present invention relates to a measuring method and a measuring apparatus that utilize attenuated total reflection, such as a surface plasmon sensor that analyzes the properties of substances, based on the generation of surface plasmon. Particularly, the present invention relates to a measuring method and a measuring apparatus that utilizes attenuated total reflection and employs p-polarized light beams.

2. Description of the Related Art

Surface plasmon sensors are known, as a type of sensor that utilizes attenuated total reflection. In metals, free electrons oscillate in groups to generate compression waves, called plasma waves. The compression waves which are generated at the surface of metals are called surface plasmon, when quantized. Various known surface plasmon sensors utilize a phenomenon, in which the surface plasmons are excited by light waves, to analyze properties of samples. Particularly well known surface plasmon sensors are those of a Kretschmann configuration (as disclosed in Japanese Unexamined Patent Publication No. 6(1994)-167443, for example).

Surface plasmon sensors of the Kretschmann configuration basically comprise: a dielectric block, shaped as a prism, for example; a metal film, formed on one surface of the dielectric block and which is brought into contact with a sample; a light source for emitting a light beam; an optical system for causing the light beam to enter the dielectric block at various angles of incidence so that total internal reflection conditions are satisfied at an interface of the dielectric block and the metal film; a photodetecting means for detecting the intensity of the light beam, which has been totally reflected at the interface; and a measuring means for measuring the state of surface plasmon resonance, based on detection results obtained by the photodetecting means.

In order to obtain various angles of incidence for the light beam, a comparatively thin incident light beam may be caused to impinge upon the interface while changing the angle of incidence. Alternatively, a comparatively thick incident light beam may be caused to impinge upon the interface in the form of convergent light or divergent light, so that the incident light beam includes components impinging upon the interface at various angles. In the former case, the light beam which is reflected from the interface at an angle, which varies as the angle of incidence changes, may be detected by a small photodetector which is moved in synchronization with the change of the angle of incidence, or by an area sensor that extends in the direction coincident with the angles of reflected light. In the latter case, an area sensor, which extends in directions such that all the components of light reflected from the interface at various angles can be detected thereby, may be employed.

In a surface plasmon sensor of the construction described above, when a light beam impinges upon the metal film at a particular angle of incidence $\theta_{sp}$ greater than or equal to the angle of total internal reflection, evanescent waves having an electric field distribution in a sample which is in contact with the metal film are generated, and surface plasmon is excited at an interface between the metal film and the sample. When the wave vector of the evanescent light is equal to the wave number of the surface plasmon and wave number matching is established, the evanescent waves and the surface plasmon resonate and light energy is transferred to the surface plasmon, whereby the intensity of light reflected in total internal reflection at the interface of the dielectric block and the metal film sharply drops. The sharp intensity drop is generally detected as a dark line by the photodetector.

The aforesaid resonance occurs only when the incident light beam is p-polarized. Accordingly, it is necessary to set the surface plasmon sensor so that the light beam enters the interface as p-polarized light. Alternatively, it is necessary to separate and detect only p-polarized light waves from the light beam, which is totally internally reflected at the interface between the dielectric block and the metal film.

When the wave number of the surface plasmon can be known from the angle of incidence $\theta_{sp}$ at which the phenomenon of attenuated total reflection (ATR) takes place, the dielectric constant of the sample can be obtained. That is, $$K_{sp}(\omega) = \frac{\omega}{c} \sqrt{\frac{\varepsilon_m(\omega)\varepsilon_s}{\varepsilon_m(\omega) + \varepsilon_s}}$$

wherein $K_{sp}$ represents the wave number of the surface plasmon, $\omega$ represents the angular frequency of the surface plasmon, c represents the speed of light in a vacuum, and $\varepsilon m$ and $\varepsilon S$ respectively represent the dielectric constants of the metal and the sample.

When the dielectric constant $\varepsilon S$ of the sample is known, the refractive index and the like of the sample can be determined on the basis of a predetermined calibration curve or the like. As a result, properties of the sample related to the refractive index, such as the dielectric constant, can be determined, by determining the angle $\theta_{sp}$ at which attenuated total reflection occurs (hereinafter, referred to as "attenuated total reflection angle $\theta_{sp}$")

As another type of sensor that utilizes attenuated total reflection, there is known a leaky mode sensor as described in, for instance, "Surface Refracto-sensor using Evanescent Waves: Principles and Instrumentations" by Takayuki Okamoto, Spectrum Researches, Vol. 47, No.1 (1998), pp. 21-23 and pp. 26-27. The leaky mode sensor basically comprises: a dielectric block, shaped as a prism, for example; a cladding layer, formed on one surface of the dielectric block; an optical waveguide layer, which is formed on the cladding layer and which is brought into contact with a sample; a light source for emitting a light beam; an optical system for causing the light beam to enter the dielectric block at various angles of incidence so that total internal reflection conditions are satisfied at an interface of the dielectric block and the cladding layer; a photodetecting means for detecting the intensity of the light beam, which has been totally reflected at the interface; and a measuring means for measuring the state of excitation of a waveguide mode, based on detection results obtained by the photodetecting means In a leaky mode sensor of the construction described above, when the light beam is caused to impinge upon the cladding layer through the dielectric block at an angle greater than or equal to an angle of total internal reflection, evanescent waves are generated in the optical waveguide layer and an evanescent wave having a particular wave number comes to propagate through the optical waveguide layer in a waveguide mode. When the waveguide mode is thus excited, almost all the incident light which generates the evanescent wave having a particular wave number is taken into the optical waveguide layer and accordingly, the intensity of light reflected in total internal reflection at the interface of the dielectric block and the clad layer sharply drops. Because the wave number of light to be propagated through the optical waveguide layer depends upon the refractive index of the sample on the optical waveguide layer, the refractive index and properties of the sample related to the refractive index can be determined, based on the attenuated total reflection angle $\theta_{sp}$.

The aforementioned surface plasmon sensors and leaky mode sensors may be utilized to perform random screening in the field of pharmaceutical manufacture. In random screening, specific substances that bond with a desired sensing substance are sought. In this case, the sensing substance is disposed on the thin film (the metal film in the case of a surface plasmon sensor, and the optical waveguide layer and the cladding layer in the case of a leaky mode sensor). Then, various solutions of test targets (sample liquids) are added to the sensing substance. Each time that a predetermined amount of time passes, the attenuated total internal reflection angle $\theta_{sp}$ is measured. If the test target binds with the sensing substance, the refractive index of the sensing substance changes over time due to the bond. Accordingly, whether the test target is bonding with the sensing substance, that is, whether the test target is the specific substance that bonds with the sensing substance, can be determined by measuring the attenuated total internal reflection angle $\theta_{sp}$ at predetermined time intervals, thereby measuring whether the attenuated total reflection angle $\theta_{sp}$ changes. A combination of an antigen and an antibody is an example of the combination of the specific substance and the sensing substance. Alternatively, a combination of an antibody and another antibody may be the combination of the specific substance and the sensing substance. Measurement regarding whether a rabbit antihuman IgG antibody, as a sensing substance, bonds with an antihuman IgG antibody, as a specific substance, and quantitative analysis of the bond, are specific examples of measurement.

Note that it is not necessary to detect the attenuated total reflection angle $\theta_{sp}$ itself, in order to measure bonding states between test targets and sensing substances. For example, a test target solution may be added to a sensing substance, then the variation in the attenuated total reflection angle $\theta_{sp}$ may be measured. The bonding state may be measured, based on the degree of the variation of the attenuated total reflection angle $\theta_{sp}$.

Cases in which the attenuated total reflection angle $\theta_{sp}$ itself is measured, and cases in which the variations in the attenuated total reflection angle $\theta_{sp}$ are measured after adding the test target solution to the sensing substance have been described. In both of these cases, it is necessary to accurately detect the central position of the dark line, that is, the position of the attenuated total reflection angle $\theta_{sp}$, at which the intensity of the light beam totally internally reflected at the interface between the dielectric block and the metal film drops sharply, in order to accurately measure the state of attenuated total reflection. However, it had been difficult to detect the position of the attenuated total reflection angle $\theta_{sp}$ with high accuracy, due to adverse influences from fluctuations in the light intensity distributions of the light beams themselves, and the like. For this reason, a measuring method and a measuring apparatus have been proposed in Japanese Unexamined Patent Publication No. 7(1995)-159319. This method and apparatus utilize the fact that attenuated total reflection occurs only when an incident light beam is p-polarized light. The method and apparatus separates a light beam, which is totally internally reflected at an interface, into p-polarized light waves and s-polarized light waves. A light intensity distribution that reflects the state of attenuated total reflection is measured utilizing the p-polarized light waves, and the light intensity distribution of the light beam itself (hereinafter, referred to as "reference light intensity distribution") is measured utilizing the s-polarized light waves. The distribution values of the light intensity distribution that reflects the state of attenuated total reflection, measured by utilizing the p-polarized light waves, are divided by the reference light intensity distribution. Thereby, the influence exerted by fluctuations in the light intensity distribution of the light beam is cancelled out. Accordingly, the position of the attenuated total reflection angle $\theta_{sp}$ is enabled to be detected with high accuracy.

However, in the above measuring method and measuring apparatus that cancels out the influence exerted by fluctuations in the light intensity distribution of the light beam, to enable highly accurate detection of the position of the attenuated total reflection angle $\theta_{sp}$, separating means for separating the totally internally reflected light beam into p-polarized light waves and s-polarized light waves is necessary. This leads to greater size and cost for the apparatus, and causes measurements to be troublesome. Further, conventional measuring methods and measuring apparatuses that utilize attenuated total reflection generally employ light sources that emit p-polarized light waves. However, in the case that the reference light intensity distribution is obtained by utilizing s-polarized light waves as described above, a light source that emits both p-polarized light waves and s-polarized light waves becomes necessary. If this type of light source is employed, the output of the p-polarized light waves is decreased, and measurement accuracy is reduced.

SUMMARY OF THE INVENTION

The present invention has been developed in view of the foregoing circumstances. It is an object of the present invention to provide a measuring method and a measuring apparatus that utilize attenuated total reflection, which are capable easily and highly accurately measuring states of attenuated total reflection, employing a miniature and low cost apparatus.

The measuring method that utilizes attenuated total reflection of the present invention comprises the steps of:

causing a p-polarized light beam to enter a measuring unit, constituted by: a dielectric block, which is transparent with respect to the p-polarized light beam; and a thin film layer, which is formed on a surface of the dielectric block and which is placed in contact with a sample, at various angles of incidence, such that total internal reflection conditions can be obtained at an interface between the dielectric block and the thin film layer;

detecting a light intensity distribution of the p-polarized light beam, which is totally internally reflected at the interface; and measuring a state of attenuated total reflection, based on the light intensity distribution;

a reference light intensity distribution of p-polarized light, in which a state of attenuated total reflection is not present, being obtained in advance;

each distribution value of the detected light intensity distribution being divided by each distribution value of the reference light intensity distribution to generate attenuated total reflection data; and the state of attenuated total reflection being measured, based on the total attenuated reflection data.

The reference light intensity distribution may be obtained by:

placing a sample, in which a state of attenuated total reflection is not present with respect to a p-polarized light beam reflected at the interface, on the thin film layer; and detecting the light intensity distribution of the p-polarized light beam which is totally internally reflected at the interface.

Alternatively, the reference light intensity distribution may be obtained by:

sequentially placing samples that exhibit different states of attenuated total reflection on the thin film layer;

sequentially detecting light intensity distributions of p-polarized light beams, which are totally internally reflected at the interface; and obtaining the reference light intensity distribution, based on the plurality of detected light intensity distributions.

The measuring apparatus that utilizes attenuated total reflection of the present invention comprises:

a measuring unit, constituted by: a dielectric block, which is transparent with respect to p-polarized light beams; and a thin film layer, which is formed on a surface of the dielectric block and which is placed in contact with a sample;

an optical system for causing a p-polarized light beam to enter the dielectric block at various angles of incidence, such that conditions for total internal reflection are obtained at an interface between the dielectric block and the thin film layer;

a photodetector for detecting light intensity distributions of the p-polarized light beam, which is totally internally reflected at the interface;

reference light intensity distribution memory means, having recorded therein a previously obtained reference light intensity distribution of p-polarized light, in which a state of attenuated total reflection is not present; and measuring means, for measuring a state of attenuated total reflection, based on the light intensity distributions, which are output from the photodetector;

the measuring means measuring the state of attenuated total reflection, by:

dividing each distribution value of the detected light intensity distribution by each distribution value of the reference light intensity distribution, to generate attenuated total reflection data; and measuring the state of attenuated total reflection, based on the total attenuated reflection data.

The reference light intensity distribution may be obtained by:

placing a sample, in which a state of attenuated total reflection is not present with respect to a p-polarized light beam reflected at the interface, on the thin film layer; and detecting the light intensity distribution of the p-polarized light beam, which is totally internally reflected at the interface, with the photodetector.

Alternatively, the reference light intensity distribution may be obtained by:

sequentially placing samples that exhibit different states of attenuated total reflection on the thin film layer;

sequentially detecting light intensity distributions of p-polarized light beams, which are totally internally reflected at the interface, with the photodetector; and obtaining the reference light intensity distribution, based on the plurality of detected light intensity distributions.

Note that the "samples" may be liquid, gas, or solid. The "samples" may be in a still state, or may be in a flowing state.

The "p-polarized light beam" refers to a light beam which has p-polarized light waves as its main components. The "p-polarized light beam" includes light beams that contain s-polarized light waves to a degree that does not obstruct measurement, that is, on the order of several %.

Further, the "sample, in which a state of attenuated total reflection is not present with respect to a p-polarized light beam reflected at the interface" refers to a sample, of which the measured attenuated total reflection angle is outside the range of various angles of incidence (that is, reflective angles) of a p-polarized light beam, when the sample is placed in contact with the thin film layer of the measuring unit and the p-polarized light beam is caused to enter the measuring unit. Note that in the case that a sensing substance is fixed on the thin film layer of the measuring unit, the sensing substance and air, or the sensing substance and a buffer liquid of a predetermined concentration functions as the "sample, in which a state of attenuated total reflection is not present with respect to a p-polarized light beam reflected at the interface".

The measuring method and the measuring apparatus that utilize attenuated total reflection according to the present invention obtains the reference light intensity distribution in advance. The reference light intensity distribution is the light intensity distribution of the p-polarized light beam which is totally internally reflected at the interface, yet does not reflect a state of attenuated total reflection. Then, each of the distribution values of the detected light intensity distribution are divided by each of the distribution values of the reference light intensity distribution, to generate attenuated total reflection data. The state of total attenuated reflection is measured, based on the attenuated total reflection data. Accordingly, a light beam constituted by p-polarized light waves can be utilized, and there is no need to provide separating means for separating the light beam totally internally reflected at the interface into p-polarized light waves and s-polarized light waves. Therefore, easy and highly accurate measurements of states of attenuated total reflection are enabled, employing a miniature and low cost apparatus.

The reference light intensity distribution may be obtained by: placing a sample, in which a state of attenuated total reflection is not present with respect to a p-polarized light beam reflected at the interface, on the thin film layer; and detecting the light intensity distribution of the p-polarized light beam which is totally internally reflected at the interface. In this case, a highly accurate reference light intensity distribution can be obtained with a single detecting operation. Note that air or buffer liquid may be utilized as the sample, in which a state of attenuated total reflection is not present with respect to the p-polarized light beam reflected at the interface. In this case, there is no need to prepare a special sample, and the reference light intensity distribution can be easily obtained.

Alternatively, the reference light intensity distribution may be obtained by: sequentially placing samples that exhibit different states of attenuated total reflection on the thin film layer; sequentially detecting light intensity distributions of p-polarized light beams, which are totally internally reflected at the interface; and obtaining the reference light intensity distribution, based on the plurality of detected light intensity distributions. In this case, there is no need to prepare a sample, in which a state of attenuated total reflection is not present with respect to the p-polarized light beam reflected at the interface. Therefore, obtainment of the reference light intensity distribution is further simplified.

BRIEF DESCRIPTION OF THE DRAWINGS

FIG. 3 is a partial sectional side view of the main parts of the surface plasmon sensor.

FIG. 4 is a schematic diagram of a flow path unit, which is employed in the surface plasmon sensor.

FIG. 5 is a block diagram that illustrates a measuring means, which is employed in the surface plasmon sensor.

DESCRIPTION OF THE PREFERRED EMBODIMENTS

Figure 1:
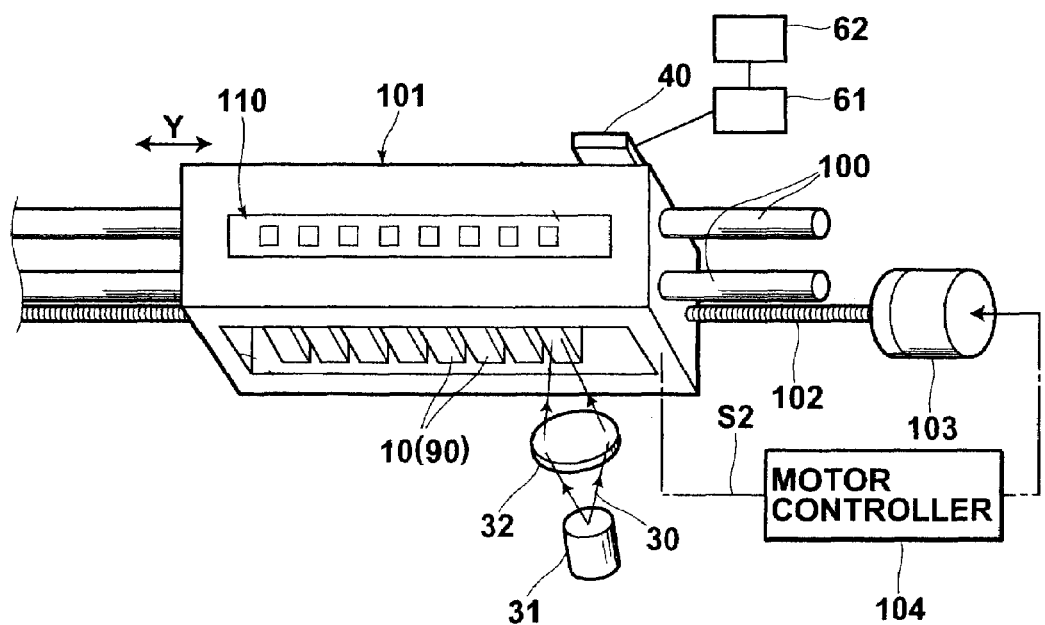
FIG. 1 is a diagram that illustrates the entire construction of a surface plasmon sensor according to a first embodiment of the present invention.
Figure 2:
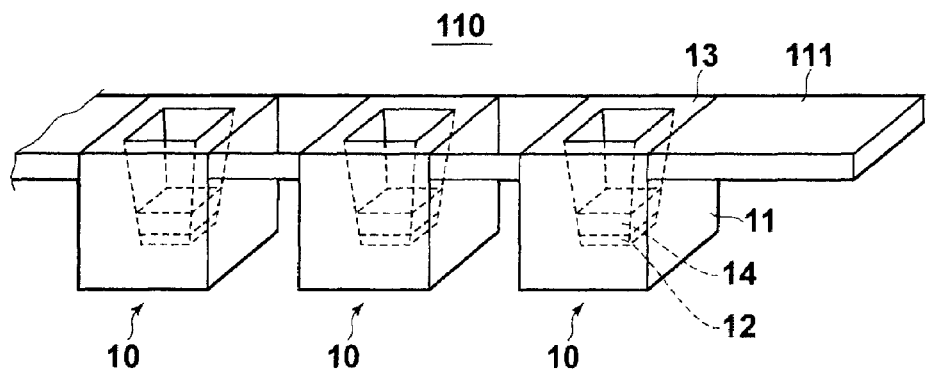
FIG. 2 is a diagram that illustrates the detailed construction of a link unit, which is employed in the surface plasmon sensor.

Hereinafter, embodiments of the present invention will be described with reference to the attached drawings. FIG. 1 is a diagram that illustrates the entire construction of a surface plasmon sensor according to a first embodiment of the present invention, to which the measuring method and the measuring apparatus that utilize attenuated total reflection of the present invention is applied. FIG. 2 is a side view that illustrates the main parts of the surface plasmon sensor.

The surface plasmon sensor measures states of bonding between sensing substances and test targets. The surface plasmon sensor measures variations in attenuated total reflection angles $\theta_{sp}$ due to surface plasmon resonance, and generates sensorgrams that represent the variation of the angles over time. After completion of bonding, measurements are also performed of states of dissociation.

As illustrated in FIG. 1, the surface plasmon sensor of the first embodiment employs a sliding block 101 as a support for measuring units. The sliding block 101 is slidably engaged with two guide rods 100, 100, which are provided parallel to each other. Thereby, the sliding block 101 is linearly slidable in the direction of arrow Y. The sliding block is in threaded engagement with a precision threaded rod 102, which is provided parallel to the guide rods 100, 100. The precision threaded rod 102 is configured to be rotated in the forward and reverse directions by a pulse motor 103. The pulse motor 103 and the precision threaded rod 102 constitute a support drive means.

Note that driving of the pulse motor 103 is controlled by a motor controller 104. That is, an output signal S2 of a linear encoder (not shown), which is built into the sliding block 101 and which detects the position of the sliding block 101 along the longitudinal direction of the guide rods 100, 100, is input to the motor controller 104, and the motor controller 104 controls the driving of the pulse motor 103 based on the signal S2.

A laser light source 31 that emits a p-polarized measuring light beam 30 (laser beam) and a condensing lens 32 that constitutes an incident optical system are provided below and to the side of the guide rods 100, 100. A photodetector 40 is provided at the side of the sliding block 101 opposite from that of the laser light source 31 and the condensing lens 32. That is, the sliding block 101 is sandwiched between the laser light source 31 and the condensing lens 32; and the photodetector 40. A measuring means 61 that receives output signals S from the two dimensional CCD imaging element 40 is connected thereto. The measuring means 61 performs processes based on the signals S, as will be described later. A display section 62 is connected to the measuring means 61.

In the present embodiment, a stick type link unit 110, in which eight measuring units 10 are linked and fixed, is employed. The measuring units 10 are set in the sliding block 101 in a state in which eight of them are arranged in a row.

FIG. 2 is a diagram that illustrates the details of the construction of the link unit 110. As illustrated in FIG. 2, the measuring units 10 are linked by linking portions 111, to form the link unit 110.

As illustrated in FIG. 2, each measuring unit 10 comprises: a dielectric block 11, which is formed substantially as a cube; and a metal film 12, which is formed on a surface (the upper surface in FIG. 2) of the dielectric block 11. The metal film 12 is formed of gold, silver, copper, or aluminum, for example.

The dielectric block 11 is formed by transparent resin, for example, and the periphery of the portion, at which the metal film 12 is formed, is raised as banks. Note that in the present embodiment, a sensing substance 14 is fixed on the metal film 12.

The condensing lens condenses the p-polarized light beam 30 such that it enters the dielectric block 11 in a convergent state, as illustrated in FIG. 3. Thereby, various angles of incidence can be achieved with respect to an interface 12a between the dielectric block 11 and the metal film 12. The range of the angles of incidence is that which includes angular ranges that enable obtainment of total internal reflection conditions at the interface 12a and that enable surface plasmon resonance.

Note that the p-polarized light beam 30 enters the interface 12a in a p-polarized state. In order to cause the light beam 30 to enter the interface 12a in a p-polarized state, the laser light source 31 may be provided such that the polarization direction thereof is in the direction of p-polarization. Alternatively, a wavelength plate or a polarizing plate may be employed to control the polarization direction of the light beam 30.

The photodetector 40 is a photodiode array, constituted by a great number of photodiodes arranged in a single row. The photodiodes are arranged in the direction indicated by arrow X of FIG. 3.

Note that pipettes and the like may be employed to supply test target solutions to the measuring units 10. Alternatively, a flow path unit 70, as illustrated in FIG. 4, may be attached to the measuring units 10, and the test target solutions may be supplied via flow paths.

The flow path unit 70 comprises: a flow path holder 71, which is formed substantially as a quadrangular pyramid having a portion cut off therefrom; a supply path 72, for supplying test target solutions; and a discharge path 73, for discharging test target solutions. The supply path 72 and the discharge path 73 are formed within the flow path holder 71. The flow path unit 70 can be easily mounted in and removed from the interior of the measuring units 10. Teflon™ tubes 74 and 75 are respectively attached to the supply path 72 and the discharge path 73. When the flow path unit 70 is mounted in the measuring unit 10, a measurement flow path 76, which is sealed by the metal film 12 and the flow path unit 70, is formed, as illustrated in FIG. 3.

A switchable pump 77 is connected to the Teflon tube 74, which is connected to the supply path 72 of the flow path unit 70. A test target solution supply path 78, a buffer liquid supply path 79, and an air supply path 80 are connected to the switchable pump 77. A liquid supply section (not shown), at which test target solutions are prepared, is connected to the test target solution supply path 78. A liquid supply section (not shown), at which buffer liquid is prepared, is connected to the buffer liquid supply path 79. The buffer liquid stored within the liquid supply section connected to the buffer liquid supply path 79 is 5% DMSO (Dimethyl Sulfoxide). An air supply section (not shown) is connected to the air supply path 80. Note that the supply sections connected to each of the supply paths are interchangeable, and are switched as necessary.

The measuring means 61 comprises: a driver 64, which is connected to the two dimensional CCD imaging element 40; and a signal processing section 65, constituted by a computer system or the like, as illustrated in FIG. 5.

As illustrated in FIG. 5, the driver 64 comprises: sample holding circuits 52a, 52b, 52c . . . , for sample holding outputs of photodiodes 40a, 40b, 40c . . . of the photodetector 40; a multiplexer 53, to which the outputs of each of the sample holding circuits 52a, 52b, 52c . . . are input; an A/D converter 54, for digitizing the output from the multiplexer 53 and inputting the digitized output to the signal processing section 65; a drive circuit 55, for driving the multiplexer 53 and the sample holding circuits 52a, 52b, 52c . . . .; and a control circuit 56, for controlling the operation of the drive circuit 55, based on commands from the signal processing section 65.

The signal processing section 65 comprises: a memory section 66, for recording therein variations R, to be described later, and a reference light intensity distribution, which is a light intensity distribution of a p-polarized light beam totally internally reflected at the interface 12a and does not reflect a state of attenuated total reflection; and an attenuated total reflection data generating section 63, for dividing each of the distribution values of light intensity distributions, which are output from the photodetector 40, by each of the distribution values of the reference light intensity distribution, which is recorded in the memory section 66, to generate attenuated total reflection data and to calculate attenuated total reflection angles $\theta_{sp}$ based thereon. Details of the reference light intensity distribution will be described later. The signal processing section 65 calculates the variation R that reflects temporal changes in attenuated total reflection angles $\theta_{sp}$, that is, temporal changes of a bonding state or a dissociating state of a sensing substance and a test target within a test target solution, at 0.5 second intervals.

Note that after a predetermined amount of time passes following initiation of measurement of the bonding state, measurement of the bonding state is completed. A sensorgram that represents changes in the variation R over time is generated. The signal processing section 65 derives a bond curve, which is a speed equation, that fit the sensorgram, based on the sensorgram. In the case that measurement is of a dissociating state, the signal processing section 65 derives a dissociating curve. Thereafter, a bonding speed constant, derived from the sensorgram, the bond curve, and the dissociation curve; and a dissociating speed constant, derived from the dissociation curve; are output to the display section 62.

Hereinafter, the operations, by which the surface plasmon sensor constructed as described above measures angular variations of attenuated total reflection angles $\theta_{sp}$, due to surface plasmon resonance, will be described. First, the sliding block 101 is moved so that a desired measuring unit 10 is placed in a measurement position. That is, the sliding block 101 is moved such that the desired measuring unit 10 is sandwiched between the laser light source 31 and the condensing lens 32, which constitutes the incident optical system, and the photodetector 40.

Prior to actual measurement, the reference light intensity distribution is obtained. The air supply path 80 is connected to the tube 74 by the switchable pump 76, and air is supplied to the measurement flow path 76 of the measuring unit 10. Note that supply of air is ceased when the measurement flow path 76 is filled with air.

The laser light source 31 is driven in this state, and the p-polarized light beam 30 emitter therefrom enters the interface 12a between the dielectric block 11 and the metal film 12 in a convergent state, as described previously. The p-polarized light beam 30, which is totally internally reflected at the interface 12a, is detected by the photodetector 40.

The photodetector 40 of the present embodiment is a photodiode array, constituted by the great number of photodiodes 40a, 40b, 40c . . . arranged in a single row. The direction that the photodiodes 40a, 40b, 40c . . . are arranged in is substantially perpendicular to the propagation direction of the p-polarized light beam 30, within the plane of the drawing sheet of FIG. 1. Accordingly, each component of the p-polarized light beam 30, which is totally internally reflected at various reflective angles at the interface 12a, is received by a different photodiode, from among the photodiodes 40a, 40b, 40c . . . .

The outputs from each of the photodiodes 40a, 40b, 40c . . . are input to the sample holding circuits 52a, 52b, 52c . . . respectively. The outputs are sample held at a predetermined timing, and then input to the multiplexer 53. The multiplexer 53 inputs the outputs of each of the photodiodes 40a, 40b, 40c . . . , which are sample held, to the A/D converter according to a predetermined order. The A/D converter digitizes the outputs, correlates each digitized output to the corresponding photodiode, and records them in the memory section 66 as the reference light intensity distribution.

Figure 6:
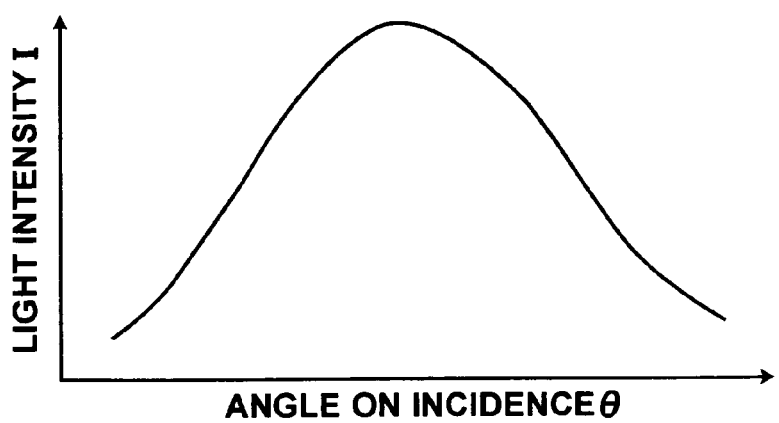
FIG. 6 is a graph that illustrates a reference light intensity distribution.

FIG. 6 is a graph for explaining the relationships among the light intensity distribution for each incident angle θ of the p-polarized light beam 30 totally internally reflected at the interface 12a and the outputs of the photodiodes 40a, 40b, 40c . . . . In the case that the measurement flow path 76 is filled with air, the attenuated total reflection angle $\theta_{sp}$ is outside the range of incident angles θ of the p-polarized light beam 30. Therefore, the light intensity distribution illustrated in FIG. 6 is a reference light intensity distribution, in which a state of attenuated total reflection is not present. Note that the substance that fills the measurement flow path 76 during obtainment of the reference light intensity distribution is not limited to air. The measurement flow path 76 may be filled with a high concentration buffer liquid (50% DMSO solution), for example.

Figure 7A:
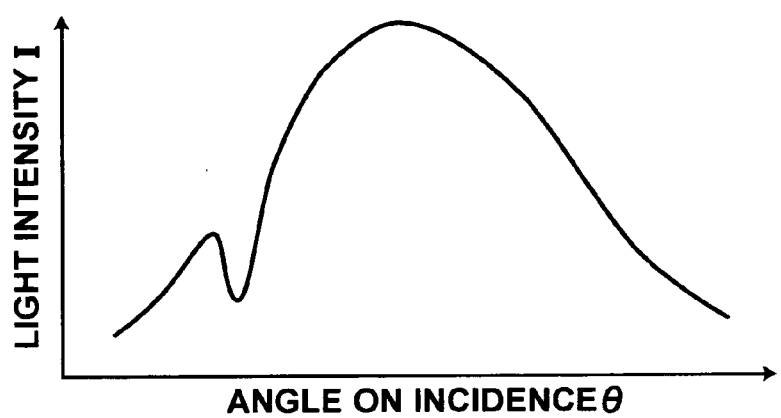
FIGS. 7A, 7B, and 7C are graphs that illustrate light intensity distributions.
Figure 7B:
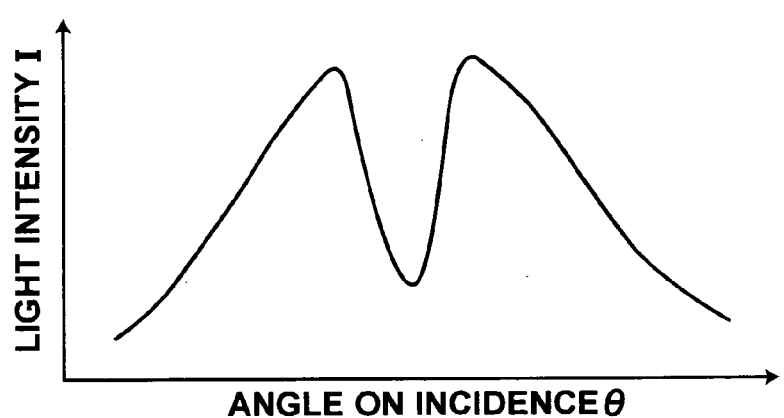
Figure 7C:
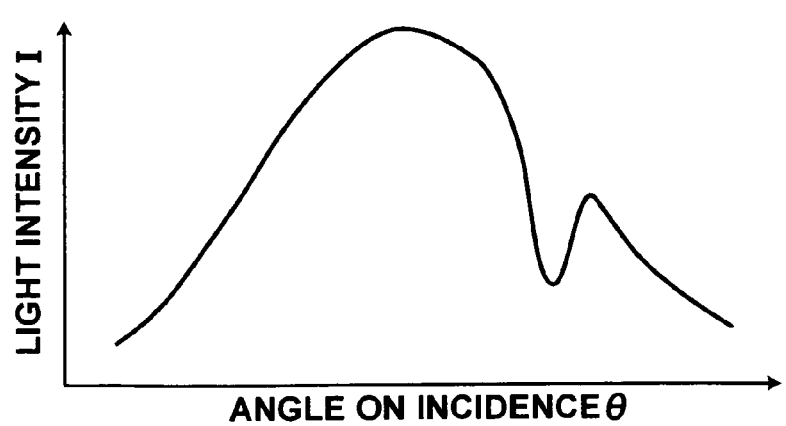
Figure 8A:
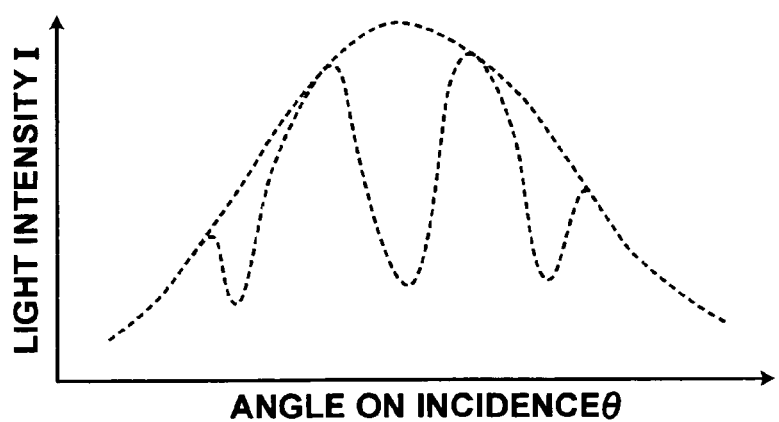
FIGS. 8A and 8B are graphs that illustrate reference light intensity distributions.
Figure 8B:
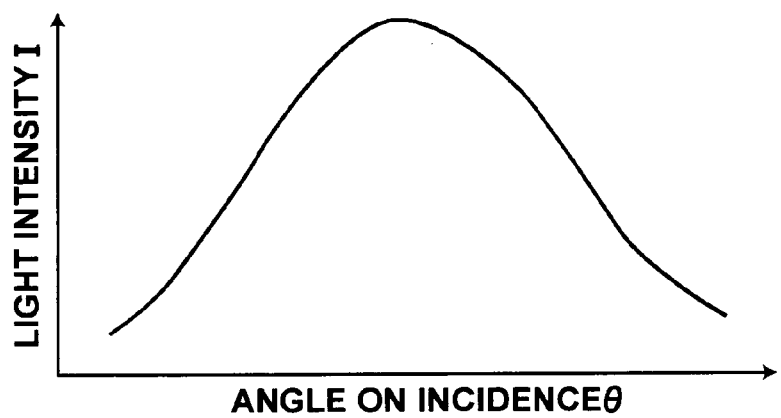

Alternatively, the reference light intensity distribution may be obtained by: sequentially filling the measurement flow path 76 with a plurality of samples that exhibit different states of attenuated total reflection; sequentially detecting light intensity distributions of p-polarized light beams 30, which are totally internally reflected at the interface 12a; and obtaining the reference light intensity distribution, based on the plurality of detected light intensity distributions. Combinations of a sensing substance and buffer liquids having different concentrations are examples of samples that exhibit different states of attenuated total reflection. A 5% DMSO solution, a 15% DMSO solution, and a 25% DMSO solution may be prepared as the buffer liquids having different concentrations. The light intensity distribution of the p-polarized light beam 30, which is totally internally reflected at the interface 12a, is obtained in states in which the measurement flow path 76 is filled with the buffer liquids of each concentration, to obtain light intensity distributions as illustrated in FIGS. 7A, 7B, and 7C. These light intensity distributions are overlapped as illustrated in FIG. 8A. Then, a reference light intensity distribution that does not reflect a state of attenuated total reflection, that is, a light intensity distribution of the p-polarized light beam 30 itself, is calculated by a fitting process, as illustrated in FIG. 8B. The reference light intensity distribution may then be recorded in the memory section 66.

Note that there are cases, in which measurements are sequentially performed employing buffer liquids of different concentrations prior to actual measurement, in order to perform bulk correction, for example. In these cases, the reference light intensity distribution may be obtained, based on the light intensity distributions which are obtained during the sequential measurements, which enables facilitated obtainment of the reference light intensity. The method of obtaining the reference light intensity by sequential measurements enables facilitated obtainment of the reference light intensity in cases that the range of incident angles θ of the p-polarized light beam 30 is great, and includes the attenuated total reflection angle $\theta_{sp}$ even when the measurement flow path 76 is filled with air or a buffer liquid of a predetermined concentration.

In addition, in cases that the reference intensity distribution is obtained based on a plurality of light intensity distributions, the reference intensity distribution may be derived by utilizing light intensity distributions, which are obtained during actual measurement. That is, the reference light intensity distribution may be sequentially updated and recorded.

Further, if the optical properties of the measuring units 10 are substantially uniform, a reference light intensity distribution, which has been obtained for a measuring unit 10 other than that which is to be employed for actual measurement, may be utilized. For example, the reference light intensity distribution may be measured and recorded in the memory section 66 prior to shipment of the measuring apparatus that utilizes attenuated total reflection of the present invention. In this case, the trouble and time necessary to obtain the reference light intensity distribution for each measurement is obviated, and measurement efficiency is improved.

Next, the operations performed during actual measurements will be described. The test target solution supply path 78 is connected to the tube 74 by the switchable pump 77, and test target solution is supplied into the measurement flow path 76 of the measuring unit 10. Note that supply of the test target solution is ceased when the measurement flow path 76 is filled with the test target solution. Measurements to follow thereafter are performed in a state in which the measurement flow path 76 is filled with the test target solution.

Measurement time t is measured by a timer (not shown), with the point in time at which the test target solution is supplied to the measuring unit 10 as a reference.

The laser light source 31 is driven in this state, in the same manner as during measurement of the reference light intensity, and the light beam 30 emitted thereby enters the interface 12a between the dielectric block 11 and the metal film 12 in a convergent state. The light beam 30, which is totally internally reflected at the interface 12a, is detected by the photodetector 40. The outputs from each of the photodiodes 40a, 40b, 40c . . . are respectively input to the sample holding circuits 52a, 52b, 52c . . . , sample held at a predetermined timing, and then input to the multiplexer 53. The multiplexer 53 inputs the outputs of each of the photodiodes 40a, 40b, 40c . . . , which are sample held, to the A/D converter according to a predetermined order. The A/D converter digitizes the outputs, correlates each digitized output to the corresponding photodiode 40a, 40b, 40c . . . and records them in the memory section 66 as a light intensity distribution.

Figure 9A:
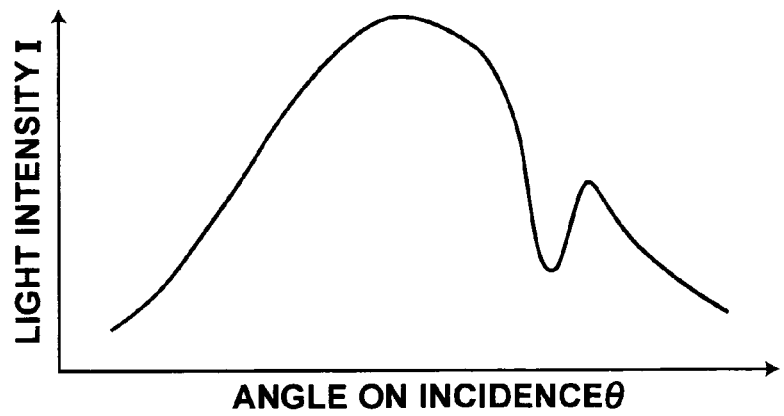
FIGS. 9A and 9B are graphs that illustrate attenuated total reflection data.

Here, the relationship among incident angles θ of the p-polarized light beam 30 with respect to the interface 12a and light intensities I is that which is illustrated in FIG. 9A. Light that enters the interface 12a at a specific incident angle $\theta_{sp}$ excites surface plasmons at an interface between the metal film 12 and the sensing substance 14. Therefore, the reflected light intensity I sharply drops for this light. That is, $\theta_{sp}$ is the attenuated total reflection angle, and the reflected light intensity I assumes its minimal value at the angle $\theta_{sp}$. The drop in the reflected light intensity I is observed as a dark line within the reflected light, as indicated by reference letter D in FIG. 3.

Figure 9B:
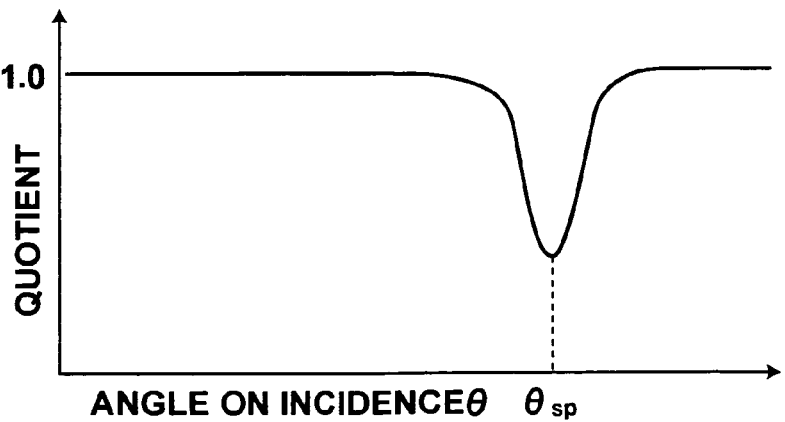
Figure 10:
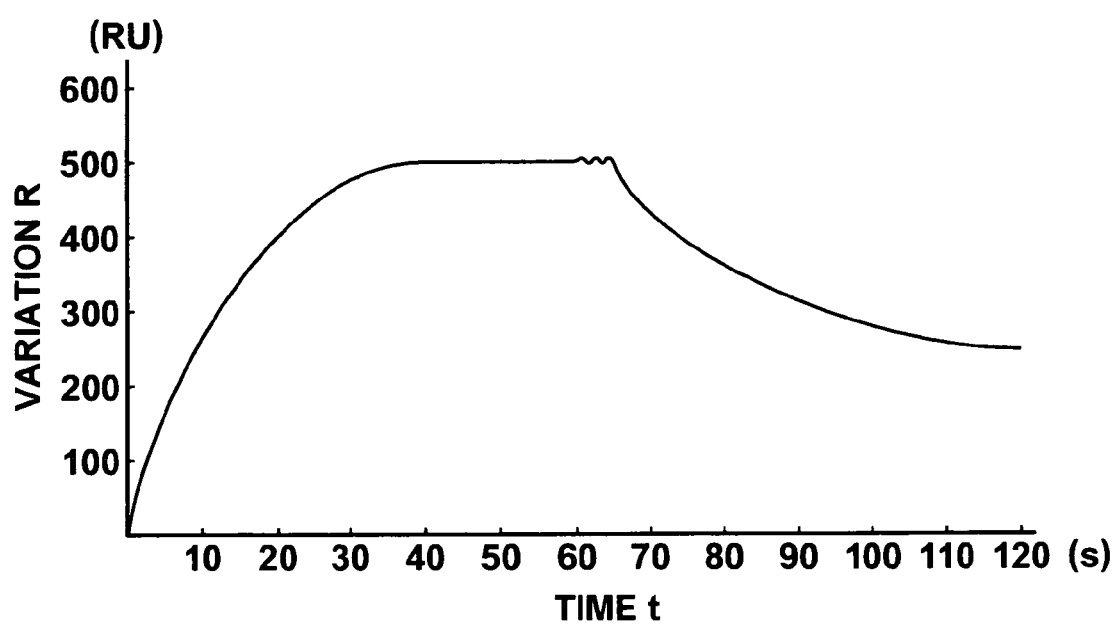
FIG. 10 is a graph that illustrates an example of a sensorgram output by the surface plasmon sensor.

The attenuated total reflection data generating section 63 of the signal processing section 65 divides each distribution value, output from each of the photodiodes 40a, 40b, 40c . . . , by distribution values of the reference light intensity distribution, as illustrated in FIG. 8B, corresponding thereto. The reference light intensity distribution is recorded in the memory section 66. Attenuated total reflection data, such as that illustrated in FIG. 9B, is generated by the division, and the attenuated total reflection angle $\theta_{sp}$ is calculated from the attenuated total reflection data. Note that at this time, the minimal value of the graph that represents the attenuated total reflection data, such as that illustrated in FIG. 9B, may be calculated. Alternatively, the median point of the depression within the graph may be calculated.

As described previously, if the test target bonds with the sensing substance 14, which is in contact with the metal film 12 of the measuring unit 10, the refractive index of the sensing substance 14 changes. Accordingly, the attenuated total reflection angle $\theta_{sp}$ also changes. Here, the attenuated total reflection angle $\theta_{sp}$, which was determined by the first measurement after the test target solution is supplied to the measurement flow path 76 of the measuring unit 10 is designated as $\theta_{sp}(0s)$. The attenuated total reflection angle $\theta_{sp}$, which is determined by a measurement performed t seconds after initiation of measurement operations, is designated as $\theta_{sp}(ts)$. The variation R of the attenuated total reflection angle $\theta_{sp}$ is defined as the difference between $\theta_{sp}(ts)$ and $\theta_{sp}(0s)$. That is, the variation R at time t is represented by the formula:

$$R = \theta_{sp}(ts) - \theta_{sp}(0s)$$

At this time, the variation R represents the change of the attenuated total reflection angle $\theta_{sp}$ over time. That is, the variation R reflects the temporal change of the bonding state between the sensing substance and the test target within the test target solution. Note that the variation R, which is determined at each measurement, is correlated with the measurement time t thereof, and recorded in the memory section 66 of the signal processing section 65. The variation R is also output to the display section 62, and a graph (sensorgram) that represents the relationship between the elapsed time t and the variation R, such as that illustrated in FIG. 8, is sequentially displayed. Note that in FIG. 8, the units of the horizontal axis (time) is seconds; and that the units of the vertical axis (variation R) are Resonance Units (RU). 1000RU corresponds to an angle of 0.1 degrees.

The signal processing section 65 completes measurements of the bonding state after a predetermined amount of time passes from the initiation of measurement of the measuring unit 10. A bond curve is derived by fitting a speed equation to the sensor grams. A bonding speed constant is obtained from the bond curve. The bond curve and the bonding speed constant are output to the display section 62. The display section 62 displays the bond curve and the bonding speed constant, in addition to the sensorgrams. Note that it is preferable that data regarding the sensing substance and the test target solution be displayed as necessary.

Next, the operations, by which dissociating states are judged when the test target solution within the measurement flow path 76 is replaced with buffer liquid, will be described. After measurement of the bonding state, the buffer liquid supply path 79 is connected to the tube 74 by the switchable pump 77, and buffer liquid is supplied to the measurement flow path 76 of the measuring unit 10. Note that supply of the buffer liquid is ceased when the measurement flow path 76 is filled with the buffer liquid. Measurements to follow thereafter are performed in a state in which the measurement flow path 76 is filled with the buffer liquid. Note that a small amount of air (bubbles) may be supplied prior to supply of the buffer liquid, and the measurement flow path 76 may be filled with the buffer liquid with the air bubbles acting as a partition between the test target solution and the buffer liquid. By partitioning the test target solution and the buffer liquid with the air bubbles, mixing of the two liquids can be prevented. This replacement may be performed by manual operations, or performed automatically, by a control means (not shown), which is connected to the measuring means 61 and the switchable pump 77.

In the case that the dissociating state is measured as well, the variation R of the attenuated total reflection angle $\theta_{sp}$ is measured every 0.5 seconds, and sensorgrams are output to the display section 62. After a predetermined amount of time passes, the display section 62 displays a dissociating curve and a dissociating speed constant as well as the sensorgrams. Note that it is preferable that data regarding the sensing substance and the test target solution be displayed as necessary.

As is clear from the above description, in the surface plasmon sensor according to the first embodiment of the present invention, the p-polarized light beam 30 is caused to enter the interface 12a. The distribution values of the light intensity distribution that reflects a state of attenuated total reflection, measured by employing p-polarized light waves, is divided by the reference light intensity distribution, measured by employing p-polarized light waves. Thereby, adverse influences due to fluctuations in the light intensity distribution of the light beam are cancelled out, enabling accurate detection of the position of the attenuated total reflection angle $\theta_{sp}$. That is, in the surface plasmon sensor according to the present invention, a light beam constituted by p-polarized light waves can be employed. Accordingly, there is no need to provide separating means for separating the light beam totally internally reflected at the interface into p-polarized light waves and s-polarized light waves. Therefore, easy and highly accurate measurements of states of attenuated total reflection are enabled, employing a miniature and low cost apparatus.

The reference light intensity distribution may be obtained by: placing a sample, in which a state of attenuated total reflection is not present with respect to the p-polarized light beam 30 reflected at the interface 12a, on the thin film layer of the measuring unit 10; and detecting the light intensity distribution of the p-polarized light beam 30 which is totally internally reflected at the interface. In this case, a highly accurate reference light intensity distribution can be obtained with a single detecting operation.

Alternatively, the reference light intensity distribution may be obtained by: sequentially placing samples that exhibit different states of attenuated total reflection on the thin film layer of the measuring unit 10; sequentially detecting light intensity distributions of p-polarized light beams 30, which are totally internally reflected at the interface 12a; and obtaining the reference light intensity distribution, based on the plurality of detected light intensity distributions. In this case, there is no need to prepare a sample, in which a state of attenuated total reflection is not present with respect to the p-polarized light beam 30 reflected at the interface. Therefore, obtainment of the reference light intensity distribution is further simplified.

Figure 11:
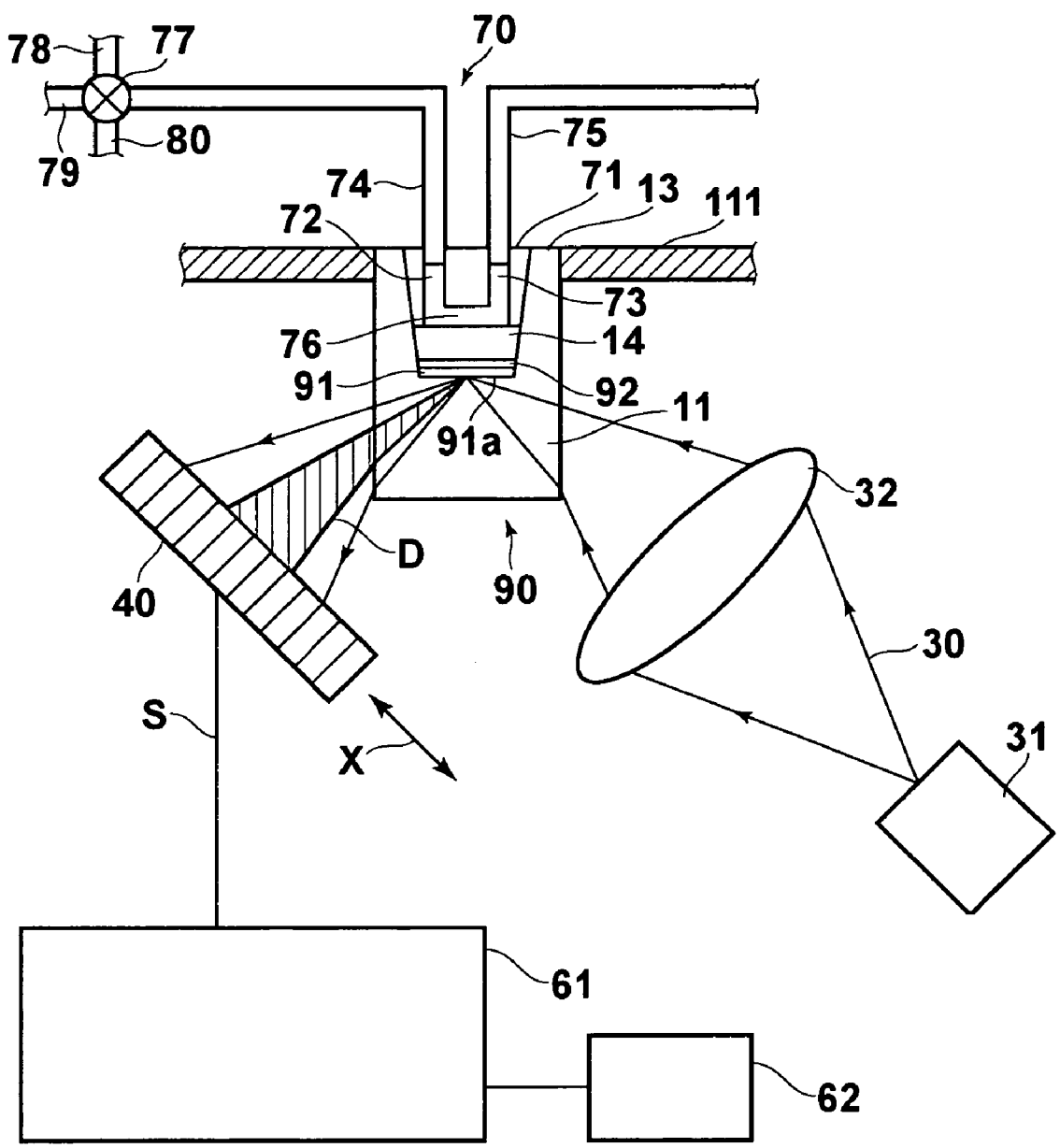
FIG. 11 is a partial sectional side view of the main parts of a leaky mode sensor according to a second embodiment of the present invention.

Next, a second embodiment of the present invention will be described with reference to FIG. 1 and FIG. 11.

The construction of the second embodiment is substantially the same as that of the first embodiment. Therefore, only one structural element that differs from that of the first embodiment is denoted with a reference number within parentheses in FIG. 1. In FIG. 11, structural elements which are the same as those illustrated in FIG. 3 are denoted with the same reference numerals, and descriptions thereof will be omitted unless particularly necessary.

The sensor that utilizes attenuated total reflection of the second embodiment is a previously described leaky mode sensor, and is configured to employ measuring units 90. A gladding layer 91 is formed on a surface (the upper surface in FIG. 11) of the dielectric block 11 of the measuring unit 90. An optical waveguide layer 92 is formed on the cladding layer 91.

The dielectric block 11 is molded from synthetic resin or optical glass, such as BK7, for example. The cladding layer 91 is formed as a thin film, from a dielectric having a lower refractive index than that of the dielectric block 11, or from a metal such as gold. The optical waveguide layer 92 is also formed as a thin film, from a dielectric having a higher refractive index than that of the cladding layer 91, such as . The film thickness of the cladding layer is approximately 36.5 nm in the case that it is formed as a thin gold film. The film thickness of the optical waveguide layer is approximately 700 nm in the case that it is formed from PMMA.

In the leaky mode sensor having the construction described above, the light beam 30 is emitted from the laser light source 30 so as to pass through the dielectric block 11 and enter the cladding layer 91. If the light beam 30 impinges on the cladding layer 91 at an incident angle greater than or equal to a total internal reflection angle, the light beam 30 is totally internally reflected at an interface 91a between the dielectric block 11 and the cladding layer 91. However, light that passes though the cladding layer 91 and enters the optical waveguide layer 92 at a specific angle and which has specific wave numbers is propagated through the optical waveguide layer 92 in a waveguide mode. When the waveguide mode is excited in this manner, most of the incident light is taken into the optical waveguide layer 92. Therefore, the intensity of the light which is totally internally reflected at the interface 91 drops sharply, that is, attenuated total reflection occurs.

The wave number of the guided light within the optical waveguide layer 92 depends on the refractive index of the sensing substance 14, which is placed on the optical waveguide layer 92. Therefore, a bonding state between the sensing substance 14 and a test target can be measured, by determining the specific incident angle at which attenuated total reflection occurs. In addition, variations R that reflect temporal changes in the states of attenuated total reflection for each measuring unit 90 can also be measured, based on output from the photodetector 40.

In the leaky mode sensor according to the first embodiment of the present invention, the p-polarized light beam 30 is caused to enter the interface 12a. The distribution values of the light intensity distribution that reflects a state of attenuated total reflection, measured by employing p-polarized light waves, is divided by the reference light intensity distribution, measured by employing p-polarized light waves. Thereby, adverse influences due to fluctuations in the light intensity distribution of the light beam are cancelled out, enabling accurate detection of the position of the attenuated total reflection angle $\theta_{sp}$. That is, in the leaky mode sensor according to the present invention, a light beam constituted by p-polarized light waves can be employed. Accordingly, there is no need to provide separating means for separating the light beam totally internally reflected at the interface into p-polarized light waves and s-polarized light waves. Therefore, easy and highly accurate measurements of states of attenuated total reflection are enabled, employing a miniature and low cost apparatus. The other advantageous effects obtained by the first embodiment can also be obtained by the second embodiment.

Note that in each of the embodiments described above, a comparatively thick p-polarized light beam including components having various angles of incidence is caused to enter the interface 12a in a convergent state. However, the present invention is not limited to such a configuration. For example, a comparatively thin p-polarized light beam may be caused to enter the interface 12a while varying the angle of incidence thereof. In this case, the reflected p-polarized light beam, of which the reflective angle changes according to the change in the incident angle, may be detected by a small photodetector that moves synchronous with the change in the reflective angle.

In addition, the photodiode array, constituted by the single row of the photodiodes 40a, 40b, 40c . . . , is employed as the photodetector in the embodiments described above. However, the present invention is not limited to such a configuration. For example, arrayed CCD imaging elements may be employed instead of the photodiodes. As another example, a two dimensional photodetector, constituted by a great number of photoelectric converting elements which are arranged two dimensionally, such as a two-dimensional CCD imaging element, may be employed. In this case, the reference light intensity distribution may be recorded two dimensionally, and the light intensity distribution value measured by each photoelectric converting element may be divided by the reference light intensity distribution to obtain the attenuated total reflection data.

What is claimed is:

1. A measuring method that utilizes attenuated total reflection, comprising the steps of:
   causing a p-polarized light beam to enter a measuring unit, constituted by:
   a dielectric block, which is transparent with respect to the p-polarized light beam; and a thin film layer, which is formed on a surface of the dielectric block and which is placed in contact with a sample, at various angles of incidence, such that total internal reflection conditions can be obtained at an interface between the dielectric block and the thin film layer;
   detecting a light intensity distribution of the p-polarized light beam, which is totally internally reflected at the interface;
   measuring a state of attenuated total reflection, based on the light intensity distribution;
   a reference light intensity distribution of p-polarized light, in which a state of attenuated total reflection is not present, being obtained in advance;
   each distribution value of the detected light intensity distribution being divided by each distribution value of the reference light intensity distribution to generate attenuated total reflection data;
   the state of attenuated total reflection being measured, based on the total attenuated reflection data; and
   storing the measured attenuated total reflection state in a memory.

2. A measuring method that utilizes total attenuated reflection as defined in claim 1, wherein:
   the reference light intensity distribution is obtained by:
   placing a sample, in which a state of attenuated total reflection is not present with respect to a p-polarized light beam reflected at the interface, on the thin film layer; and
   detecting the light intensity distribution of the p-polarized light beam which is totally internally reflected at the interface.

3. A measuring method that utilizes total attenuated reflection as defined in claim 1, wherein:
   the reference light intensity distribution is obtained by:
   sequentially placing samples that exhibit different states of attenuated total reflection on the thin film layer;
   sequentially detecting light intensity distributions of p-polarized light beams, which are totally internally reflected at the interface; and
   obtaining the reference light intensity distribution, based on the plurality of detected light intensity distributions.

4. The method of claim 1, further comprising determining characteristics of the sample based on the stored attenuated total reflection state in the memory.

5. The method of claim 1, wherein the reference light intensity distribution is based on a p-polarized light without separation of the s-polarized light.

6. A measuring apparatus that utilizes total attenuated reflection, comprising:
   a measuring unit, constituted by:
   a dielectric block, which is transparent with respect to p-polarized light beams; and
   a thin film layer, which is formed on a surface of the dielectric block and which is placed in contact with a sample;
   an optical system for causing a p-polarized light beam to enter the dielectric block at various angles of incidence, such that conditions for total internal reflection are obtained at an interface between the dielectric block and the thin film layer;

a photodetector for detecting light intensity distributions of the p-polarized light beam, which is totally internally reflected at the interface;

reference light intensity distribution memory means, having recorded therein a previously obtained reference light intensity distribution of p-polarized light, in which a state of attenuated total reflection is not present; and measuring means, for measuring a state of attenuated total reflection, based on the light intensity distributions, which are output from the photodetector;

the measuring means measuring the state of attenuated total reflection, by:

dividing each distribution value of the detected light intensity distribution by each distribution value of the reference light intensity distribution, to generate attenuated total reflection data; and measuring the state of attenuated total reflection, based on the total attenuated reflection data.

7. A measuring apparatus that utilizes total attenuated reflection as defined in claim 6, wherein:

the reference light intensity distribution is obtained by:

placing a sample, in which a state of attenuated total reflection is not present with respect to a p-polarized light beam reflected at the interface, on the thin film layer; and detecting the light intensity distribution of the p-polarized light beam which is totally internally reflected at the interface.

8. A measuring apparatus that utilizes total attenuated reflection as defined in claim 6, wherein:

the reference light intensity distribution is obtained by:

sequentially placing samples that exhibit different states of attenuated total reflection on the thin film layer;

sequentially detecting light intensity distributions of p-polarized light beams, which are totally internally reflected at the interface; and obtaining the reference light intensity distribution, based on the plurality of detected light intensity distributions.

9. A measuring apparatus that utilizes total attenuated reflection, comprising:

a measuring unit, constituted by:
a dielectric block, which is transparent with respect to p-polarized light beams;
a cladding layer formed on a surface of the dielectric block;
an optical waveguide layer formed on the cladding layer; and
a thin film layer, which is formed on a surface of the optical waveguide layer and which is placed in contact with a sample;

an optical system for causing a p-polarized light beam to enter the dielectric block at various angles of incidence, such that conditions for total internal reflection are obtained at an interface between the dielectric block and the thin film layer;

a photodetector for detecting light intensity distributions of the p-polarized light beam, which is totally internally reflected at the interface;

reference light intensity distribution memory means, having recorded therein a previously obtained reference light intensity distribution of p-polarized light, in which a state of attenuated total reflection is not present; and measuring means, for measuring a state of attenuated total reflection, based on the light intensity distributions, which are output from the photodetector;

the measuring means measuring the state of attenuated total reflection, by:

dividing each distribution value of the detected light intensity distribution by each distribution value of the reference light intensity distribution, to generate attenuated total reflection data; and measuring the state of attenuated total reflection, based on the total attenuated reflection data.

10. The measuring apparatus according to claim 9, wherein the cladding layer and the optical waveguide layer are formed of a dielectric material.

11. The measuring apparatus according to claim 10, wherein a refractive index of the cladding layer is lower than a refractive index of the dielectric block and a refractive index of the optical waveguide layer is higher than the refractive index of the cladding layer.

* * * * *